United States Patent [19]

Sawaki et al.

[11] 3,972,899
[45] Aug. 3, 1976

[54] α-PYRONE DERIVATIVES

[75] Inventors: Mikio Sawaki; Isao Iwataki, both of Odawara; Hisao Ishikawa, Oiso; Shozo Yamada, Hiratsuka; Yasushi Yasuda, Fujisawa, all of Japan

[73] Assignee: Nippon Soda Company Limited, Tokyo, Japan

[22] Filed: Nov. 9, 1973

[21] Appl. No.: 414,300

Related U.S. Application Data

[63] Continuation-in-part of Ser. No. 347,790, April 4, 1973.

[30] Foreign Application Priority Data

Nov. 24, 1972 Japan.............................. 47-117141

[52] U.S. Cl................................. 260/343.5; 71/88; 260/345.9; 424/279
[51] Int. Cl.².................... A01N 9/20; C07D 309/38
[58] Field of Search................................ 260/343.5

[56] References Cited
UNITED STATES PATENTS 2,681,916   6/1954   Gysin et al...................... 260/343.5

FOREIGN PATENTS OR APPLICATIONS 7,305,083   10/1973   Netherlands

Primary Examiner—Jane S. Myers
Attorney, Agent, or Firm—George B. Oujevolk

[57] ABSTRACT

Compounds of the formula

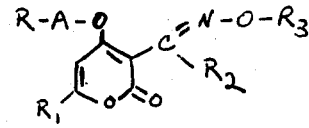

wherein $R_1$ and $R_2$ are alkyl having 2 to 6 carbon atoms or phenyl; $R_3$ is alkyl having 1 to 10 carbon atoms, alkenyl or alkynyl having up to six carbon atoms; R is alkyl of 1 to 20 carbon atoms, phenyl or phenyl substituted with halogen, methyl, methoxy or nitro; and A is carbonyl or sulfonyl, are effective as herbicides, plant growth regulators and fungicides.

5 Claims, 8 Drawing Figures

α-PYRONE DERIVATIVES

This is a continuation-in-part application of Ser. No. 347,790 filed Apr. 4, 1973.

The present invention relates to novel compounds of α-pyrone derivatives, a process for the preparation thereof and their uses as herbicides having selective activity and plant growth regulator.

Further, this invention relates to herbicidal and plant growth regulating compositions containing one or more of novel compounds, and to the method of combatting weeds and regulating the plant growth which comprises applying to plant or to soil the said compounds.

In addition to the above-mentioned effects the compounds of the present invention show fungicidal activity.

It is an object of the present invention to prepare α-pyrone derivatives and metal salts thereof.

Another object is to prepare improved compositions and processes for killing undesired plants.

The inventors synthesized quite a few compound of α-pyrone derivatives and tested the biological activities for the compounds.

As the result of the test, it has been discovered that the new and novel compounds of the present invention are particularly effective as herbicides, plant growth regulators and fungicides.

The novel compounds of this invention are characterized by the following formula:

wherein
$R_1$ is alkyl having 2 to 6 carbon atoms or phenyl;
$R_2$ is alkyl having 2 to 6 carbon atoms or phenyl;
$R_3$ is alkyl having 1 to 10 carbon atoms or alkenyl having 6 or less carbon atoms or alkynyl having 6 or less carbon atoms;
R is alkyl having 1 to 20 carbon atoms or phenyl or phenyl substituted with halogen, methyl, methoxy or nitro group;
A is carbonyl or sulfonyl.

The compounds are particularly effective as selective herbicides for grass weeds such as annual bluegrass (*Poa annua*), water foxtail (*Alopecurus aequalis*), large crab-grass (*Digitaria adscendens*) and others, especially it has now been found that the compounds hardly injure leguminous plants such as adzuki bean (*phaseolus angularis*) and soy bean (*Glycine max*) and broad leaf plants such as sugar beets which easily suffer phyto-toxicity. The compound of this invention can be applied directly to the soil as pre-emergence treatments or as post-emergence treatment to plant foliage, or they can be mixed intimately with the soil.

It is already known that 4-hydroxy-6-methyl-α-pyrone derivatives has herbicidal properties as shown in Japanese Patent Publication No. 16916/1971.

But in order to wither completely to death the said grass weeds, a large amount of the above herbicidal chemical is required and this is one drawback for above mentioned herbicidal compound.

In the other words, according to the description of above mentioned public patent bulletin and the results of the latter additional experiments by the inventors, a chemical amount containing 500 g of effective ingredient, in proportion to 10 a. of area is able to give an expected effect in the case of employing it practically, but another chemical amount containing 250 g of effective ingredient, in proportion to 10 a. of area is not able to wither grass weeds to death, in the other words, it cannot give a perfect herbicidal effect.

But, in the event of employing the compound of the present invention as a herbicide, a chemical amount containing 250 g of effective component, as a matter of course, further a chemical amount containing 125 g of less of effective ingredient, in proportion to 10 a. of area, in compliance with the same treating method of conventional herbicide indicates a strong herbicidal effect effect and thereby a perfect prevention and extermination of weeds can be expected.

In case of foliar treatment using the compounds of the present invention, even the same amount of chemical which makes barnyard grass of grass weeds completely kill gives no damages to broadleaf plants such as radish, soy bean (*Glycine max*), garden pea (*Pisum sativum*), spinach (*Spinacia oleracea*) sugar beets and carrot at all, and in case of soil treatment before germination, even the same amount of chemicals which prevents large carb-grass (*Digitaria adscendens*) germinating gives no damages to seeds of broad leaf plants at all.

As mentioned above, a secure safety to the broadleaf crop against phytotoxicity of the herbicide is extremely high and as to its application, in the other words, its applicable time, its applying location and its applying concentration, it has a very broad extent and it can be used in the wider extent.

It has been further found that the new compounds of the present invention have both dwarfing effect which control the excess growth of perennial plant, particularly lawn and inhibition effect of heading.

Though lawn which is one of industrial crops is widely grown in gardens and golf rinks, it is very troublesome to trim it well, particularly in summer lawn grows well, a large labor power is employed for mowing it and further heading spoils remarkably it's beautiful sight.

The compounds of the said general formula can be applied to the soil or leaves, and show the dwarfing effects, inhibitions of heading and runner for lawn without injury.

The compounds of the present invention shows plant growth regulating effect of controlling the growth of new buds without giving any damages to developing leaves and stems of broad leaf crops when the compounds are used in greater quantities that the compounds are used to have the effects of killing weeds and the activity of selective herbicides for broad leaf crops.

Growth inhibiting effect for new buds of broad leaf crops prevents the growth of auxiliary buds of tobacco or chrysanthemum, stops useless nutritive growth of fruit-trees or beans and further change the said growth to reproductive growth. These controlling effects are very useful for cultivating crops.

It is another advantage of the present invention that a residual toxicity in the soil or the plant and an acute toxicity for warm blooded animals and fishes are not feared because the said compounds can be employed with a low chemical concentration.

The compounds of this invention can be prepared in accordance with the following equation:

(I)     (II)     (III)     (IV)

wherein $R_1$, $R_2$, $R_3$, R and A represent the aforesaid meanings and X represents halogen atom. With respect to the above formula (I) it is expected that the said compound has the following three chemical formulae because of tautomerism The starting material (I) can be prepared in accordance with the following equation:

(V)     (VI)     (I)

wherein $R_1$, $R_2$ and $R_3$ represent the aforesaid meanings.

Hydrogen and oxygen in the compound (I) is favourably located so that the proton forms hydrogen bond as shown in the formula (VII).

(VII)

Owing to the above intramolecular hydrogen bond, the compounds of the present invention cannot be obtained under the normal reaction conditions such as acylation using acid anhydride or acylchloride together with tertiary amine, because the by-product is obtained or pyrane ring is cleavaged.

After many kinds of experiments and investigations, it was discovered that the compounds of this invention are obtained in satisfactory high yields when compound (VII) is treated with alkali hydroxide such as sodium hydroxide or potassium, protone of the hydrogen bond of (VII) is substituted with metal atom as indicated (VII).

(VIII)

and after that, compound VIII is reacted with compound (II) or (III).

As substituted metals in the formula (VIII), sodium, potassium, calcium, barium, manganese and silver are used, preferably alkali metal such as sodium or potassium are used because of their cheap price for industrial productions.

In practical method the compounds of this invention are prepared through the reaction of general formula (II) or (III) with the general formula (I) which is dissolved in inert solvent, further alkali hydroxide such as sodium hydroxide or potassium hydroxide is added to the mixture and thereby the alkali metal salt of the general formula (I) is prepared.

The said alkali metal salt after taking up from the reaction mixture is made to react with the compound having the general formula (II) or (III), otherwise, the said alkali metal salt in the reaction mixture is made to react directly with it.

As the above inert solvent, acetone, ether, benzene, chloroform, acetonitrile, dichloroethane, dichloromethane, ethyl acetate, dioxane, toluene, xylene and acetic acid etc. are used, but preferably, benzene, ether and dry acetone are used.

Reaction temperature is from −10°C to the boiling point of employed solvent, preferably from −10° to 30° and the reaction terminates between 20 minutes and several hours.

After the reaction is terminated, the crude product is isolated from the reaction mixture by extraction with solvent or by washing after distillation of the solvent.

In case of crystalline substance, the crude product can be purified by recrystallization and in oily substance the crude product can be purified by distillation or isolation by column chromatography.

A chemical structure for the resulting purified compound can be confirmatively identified by means of an elementary analysis, NMR spectrum and IR spectrum.

Figure 1:
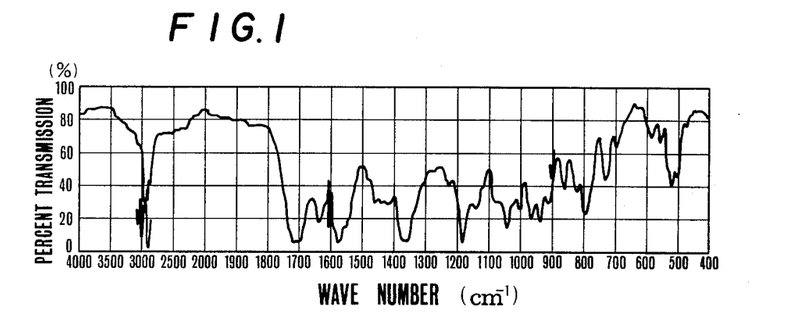
FIG. 1 is the infrared spectrum of compound No. 3
Figure 2:
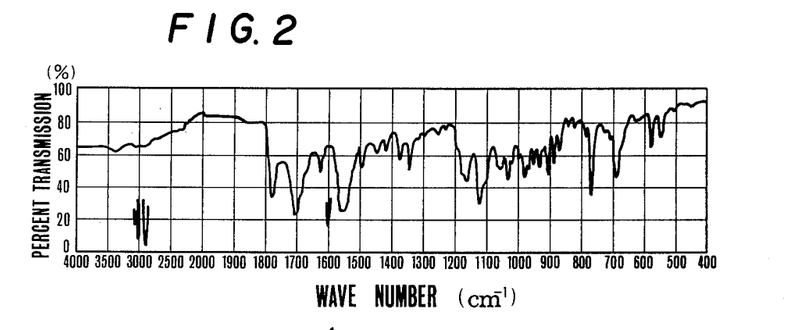
FIG. 2 is the infrared spectrum of compound No. 7
Figure 3:
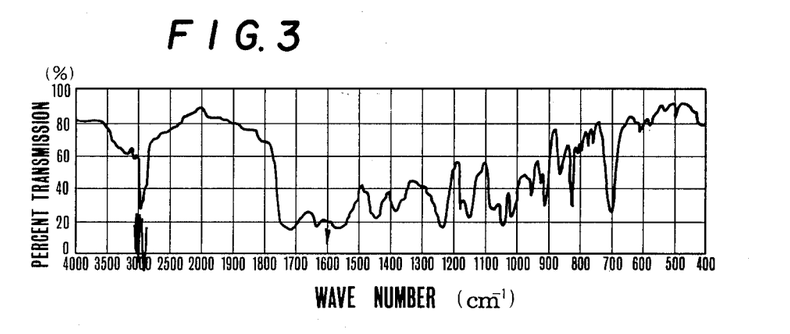
FIG. 3 is the infrared spectrum of compound No. 13
Figure 4:
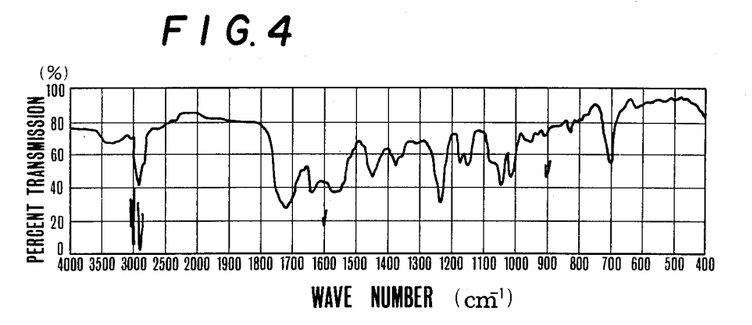
FIG. 4 is the infrared spectrum of compound No. 16
Figure 5:
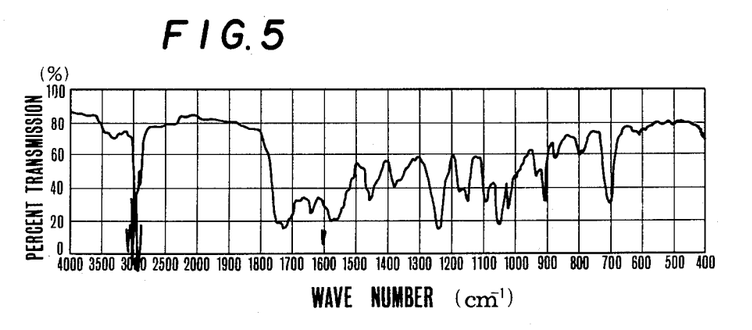
FIG. 5 is the infrared spectrum of compound No. 17
Figure 6:
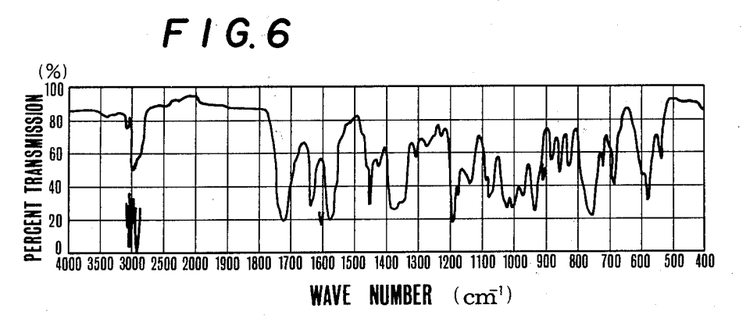
FIG. 6 is the infrared spectrum of compound No. 20
Figure 7:
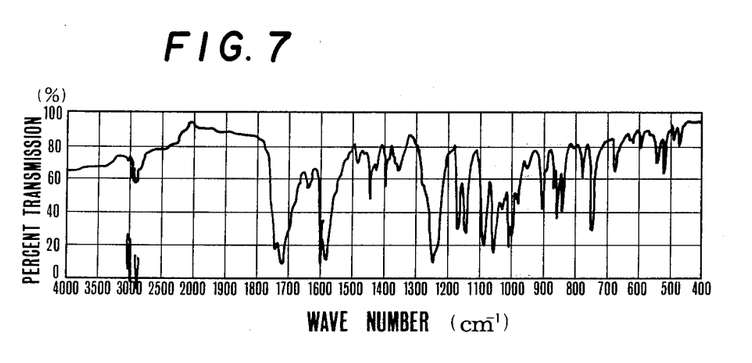
FIG. 7 is the infrared spectrum of compound No. 23
Figure 8:
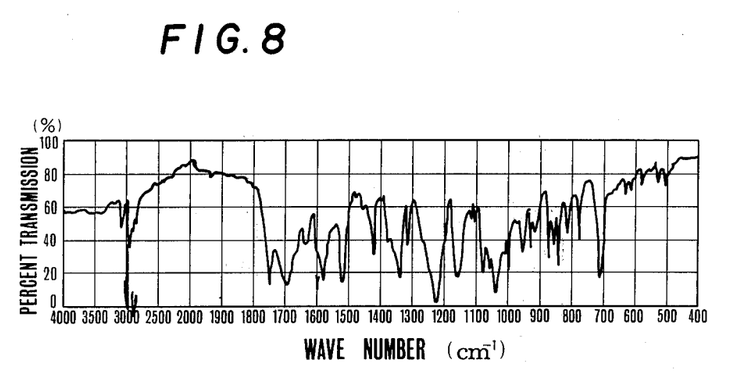
FIG. 8 is the infrared spectrum of compound No. 35

In order to facilitate a clear understanding of the invention, the following preferred specific embodiments are described as illustrative and not as limiting the invention.

EXAMPLE 1.

3-(N-ethoxypropionimidoyl)-6-ethyl-4-methanesulfonyloxy-α-pyrone 2.39 g (0.01 mol) of 3-[1-(N-ethoxyamino)-propylidene]-6-ethyl-3,4-dihydro-2H-pyran-2,4-dione was dissolved in 20 c.c. of acetone and 2 c.c. of aqueous solution containing 0.4 g (0.01 mol) of dissolved caustic soda was added in above resulting solution at room temperature under agitating step. Then, the resulting solution was cooled and 1.5 g (0.01 mol) of methanesulfonyl chloride was dropped in it at a temperature ranging from −5° to 0°C. The resulting solution was agitated during about 15 minutes immediately after having finished the dropping step and further, it was agitates at room temperature during a time of 20–30 minutes. After finishing the reaction, the said acetone was distilled off from the reaction mixture under a reduced pressure. Then, 20 c.c. of chloroform was added and dissolved in a residual material. The resulting chloroform layer was rinsed with 10 c.c. of aqueous solution containing two weight percent concentration of caustic soda and then, it was rinsed with 10 c.c. of water. The said chloroform layer was dried with magnesium sulfate. The chloroform solution was filtered and chloroform is distilled off under a reduced pressure and thereby, 3-(N-ethoxypropionimidoyl)-6-ethyl-4-methanesulfonyloxy-α-pyrone was obtained as a colorless, viscous liquid.

Yield was 2.5 g (79%) and refractive index was $n_D^{24}$ 1.5187.

EXAMPLE 2

3-(N-allyloxybutylimidoyl)-6-methyl-4-propionyloxy-α-pyrone 2.5 g (0.01 mol) of a dry sodium salt of 3-[1-(N-allyloxyamino)butylidene]-6-methyl-3,4-dihydro-2H-pyrane-2,4-dione was suspended in 30 c.c. of ether and then, 0.92 g (0.01 mol) of propionyl chloride was dropped in the resulting liquid suspension at a temperature ranging from −5° or 0°C under a simultaneous agitating step. After having finished the dropping step, the liquid suspension was continuously agitated during about 10 minutes and further, it was agitated during 3 hours at room temperature and then, a reaction was carried out during 1 hour under a simultaneous refluxing step. After cooling it, the resulting cyrstal was filtered off from it, and the resulting ether layer was rinsed with 10 c.c. of aqueous solution containing 2% of dissolved caustic soda and further, it was rinsed with 10 c.c. of water; and then, the said ether layer was dried with magnesium sulfate. The ether solution was filtered and the ether was distilled off under a reduced pressure and thus, 3-(N-allyloxybutylimidoyl)-6-methyl-4-propionyloxy-α-pyrone was obtained as a colorless, viscous liquid.

Yield was 2.45 g (80%) and refractive index was $n_D^{24}$ 1.5154.

EXAMPLE 3

4-Benzoyloxy-3-(N-ethoxypropionimidoyl)-6-methyl-α-pyrone

The same reaction procedures in Example 1 were carried out by using 2.25 g (0.01 mol) of 3-[1-(N-ethoxyamino)propylidene]-6-methyl-3,4-dihydro-2H-pyran-2,3-dione and 0.4 g (0.01 mol) of caustic soda and 1.45 g (0.01 mol) of benzoyl chloride and thereby, 4-benzoyloxy-3-(N-ethoxypropionimidoyl)-6-methyl-α-pyrone was obtained as a colorless, viscous liquid.

Yield was 3.1 g (94%) and refractive index was $n_D^{28}$ 1.5539.

EXAMPLE 4

4-(4-chlorobenzoyloxy)-3-(N-ethoxypropionimidoyl)-6-ethyl-α-pyrone

The same reaction procedures in Example 1 were carried out by using 2.39 g (0.01 mol) of 3-[1-(N-ethoxyamino)propylidene]-6-ethyl-3,4-dihydro-2H-pyran-2,4-dione and 0.4 g (0.01 mol) of caustic soda and 1.75 g (0.01 mol) of 4-chlorobenzoyl chloride and then, a solvent used for the extraction was distilled off and the reaction compound was recrystallized with n-hexane and thereby, 4-(4-chlorobenzoyloxy)-3-(N-ethoxypropionimidoyl)-6-ethyl-α-pyrone was obtained as a colorless, plate crystal.

Yield was 3.3 g (88%) and melting point was 57° to 59°C.

In addition to the above mentioned compounds described in the preceding examples, some typical compounds of the present invention are listed in Table 1.

Table 1

| Compound No. | A-R | $R_1$ | $R_2$ | $R_3$ | Physical Constant |
|---|---|---|---|---|---|
| 1 | $COCH_3$ | $CH_3$ | $C_3H_7$ | $CH_2CH=CH_2$ | $n_D^{23.5}$ 1.5192 |
| 2 | $COCH_3$ | $C_2H_5$ | $C_2H_5$ | $C_2H_5$ | $n_D^{24.5}$ 1.5117 |
| 3 | $SO_2CH_3$ | $C_2H_5$ | $C_2H_5$ | $C_2H_5$ | $n_D^{24.5}$ 1.5187 |
| 4 | $COC_2H_5$ | $CH_3$ | $C_3H_7$ | $CH_2CH=CH_2$ | $n_D^{24}$ 1.5154 |
| 5 | $COC_2H_5$ | $C_2H_5$ | $C_2H_5$ | $C_2H_5$ | $n_D^{24}$ 1.5105 |
| 6 | $COC_2H_5$ | $C_2H_5$ | $C_2H_5$ | $CH(CH_3)_2$ | $n_D^{19}$ 1.5055 |
| 7 | $COC_2H_5$ | C₆H₅ | C₆H₅ | $CH_2CH=CH_2$ | 102–104°C |
| 8 | $SO_2C_2H_5$ | $C_2H_5$ | $C_2H_5$ | $C_2H_5$ | $n_D^{24}$ 1.5101 |
| 9 | $COCH(CH_3)_2$ | $C_2H_5$ | $C_2H_5$ | $C_2H_5$ | $n_D^{24.5}$ 1.5009 |
| 10 | $CO(CH_2)_4CH_3$ | $CH_3$ | $C_3H_7$ | $CH_2CH=CH_2$ | $n_D^{25.5}$ 1.4970 |
| 11 | CO-C₆H₅ | $CH_3$ | $C_2H_5$ | $C_2H_5$ | $n_D^{28}$ 1.5539 |

Table 1-continued

| Compound No. | A-R | $R_1$ | $R_2$ | $R_3$ | Physical Constant |
|---|---|---|---|---|---|
| 12 | CO–⟨phenyl⟩ | $CH_3$ | $C_3H_7$ | $CH_2CH=CH_2$ | $n_D^{26}$ 1.5590 |
| 13 | CO–⟨phenyl⟩ | $C_2H_5$ | $C_2H_5$ | $C_2H_5$ | $n_D^{26}$ 1.5515 |
| 14 | CO–⟨phenyl⟩ | $C_2H_5$ | $C_2H_5$ | $CH_2CH=CH_2$ | $n_D^{26}$ 1.5514 |
| 15 | CO–⟨phenyl⟩ | $C_2H_5$ | $C_2H_5$ | $C_4H_9$ | $n_D^{27.5}$ 1.5462 |
| 16 | CO–⟨phenyl⟩ | $C_2H_5$ | $C_2H_5$ | $C_6H_{13}$ | $n_D^{22.5}$ 1.5310 |
| 17 | CO–⟨phenyl⟩ | $C_3H_7$ | $C_3H_7$ | $C_2H_5$ | $n_D^{24}$ 1.5406 |
| 18 | CO–⟨phenyl⟩ | $C_3H_7$ | $C_3H_7$ | $CH_2CH=CH_2$ | $n_D^{23}$ 1.5405 |
| 19 | $SO_2$–⟨phenyl⟩ | $CH_3$ | $C_2H_5$ | $C_2H_5$ | $n_D^{28}$ 1.5506 |
| 20 | $SO_2$–⟨phenyl⟩ | $C_2H_5$ | $C_2H_5$ | $CH_2CH=CH_2$ | $n_D^{26}$ 1.5504 |
| 21 | CO–⟨phenyl⟩–Cl | $C_2H_5$ | $C_2H_5$ | $CH_3$ | 85–87°C |
| 22 | CO–⟨phenyl⟩–Cl | $CH_3$ | $C_2H_5$ | $C_2H_5$ | 65–67°C |
| 23 | CO–⟨phenyl⟩–Cl | $CH_3$ | $C_3H_7$ | $CH_2CH=CH_2$ | 78–79°C |
| 24 | CO–⟨phenyl⟩–Cl | $C_2H_5$ | $C_2H_5$ | $C_2H_5$ | 57–59°C |
| 25 | CO–⟨phenyl⟩–Cl | $C_3H_7$ | $C_2H_5$ | $C_2H_5$ | $n_D^{24.5}$ 1.5573 |
| 26 | $SO_2$–⟨phenyl⟩–Cl | $C_3H_7$ | $C_3H_7$ | $C_2H_5$ | $n_D^{23.5}$ 1.5525 |
| 27 | CO–⟨phenyl⟩–$CH_3$ | $CH_3$ | $C_3H_7$ | $CH_2CH=CH_2$ | $n_D^{24}$ 1.5559 |
| 28 | $SO_2$–⟨phenyl⟩–$CH_3$ | $C_2H_5$ | $C_2H_5$ | $CH_2C\equiv CH$ | $n_D^{24}$ 1.5591 |
| 29 | $SO_2$–⟨phenyl⟩–$CH_3$ | $C_2H_5$ | $C_2H_5$ | $C_4H_9$ | $n_D^{27.5}$ 1.5444 |
| 30 | $SO_2$–⟨phenyl⟩–$CH_3$ | $C_2H_5$ | $C_3H_7$ | $C_2H_5$ | 38–39°C |
| 31 | CO–⟨phenyl-$OCH_3$ (ortho)⟩ | $C_2H_5$ | $C_2H_5$ | $C_2H_5$ | $n_D^{23.5}$ 1.5653 |
| 32 | CO–⟨phenyl-$OCH_3$ (meta)⟩ | $CH_3$ | $C_3H_7$ | $CH_2CH=CH_2$ | $n_D^{24.5}$ 1.5619 |
| 33 | CO–⟨phenyl-$OCH_3$ (meta)⟩ | $C_2H_5$ | $C_2H_5$ | $C_2H_5$ | 63–65°C |
| 34 | CO–⟨phenyl-$NO_2$ (meta)⟩ | $C_2H_5$ | $C_2H_5$ | $C_2H_5$ | 85–88°C |
| 35 | CO–⟨phenyl⟩–$NO_2$ | $C_2H_5$ | $C_2H_5$ | $C_2H_5$ | 103–105°C |

Hereinafter, the compounds of this invention are represented by Compound No. in Table 1.

The compounds of this invention can be applied directly to the soil as pre-emergence treatment or as post-emergence treatment and to plant foliage or they can be mixed intimately with the soil and may be applied to soil or foliar at rates of 50–1000 g per area, preferably 100–500 g per area, more preferably 200–300 g per area.

The method of the present invention comprehends the employment of a liquid or solid composition containing one or more of the present compounds as an active ingredient.

The active ingredient of this invention may be formulated by mixing with suitable carriers in a form generally used in agricultural chemicals such as wettable powder, emulsifiable concentrate, dust formulation, granular formulation, water soluble powder and aerosol. As solid carriers, bentonite, diatomaceous earth, apatite, gypsum, talc, pyrophyllite, vermiculite, clay and others are used. As liquid carriers, kerosene, mineral oil, petroleum, solvent naphtha, benzene, xylene, cyclohexane, cyclohexanone, dimethylformamide, alcohol, acetone, and others are used. Sometimes surface active agent is added in order to give a homogeneous and stable formulation.

The compounds of this invention also can be applied admixed with other chemicals which are used in agronomic and horticultural management and are compatible with the compounds of this invention. Such chemicals can be, but are not restricted to, the classes of chemicals commonly known as plant nutrients, fertilizers, insecticides, acaricides, fungicides, herbicides and nematocides.

As for known herbicide it is recommended that the compound of the present invention is applied admixed with urea derivatives such as Linuron or DCMU, triazine derivatives such as Atrazine or Simazine and amide derivatives such as NPA.

The concentrations of the active ingredients in the herbicidal and plant growth regulating composition of this invention vary according to type of formulation, and they are, for example, used in a range of 5–80 weight percent, preferably 20–80 weight percent, in wettable powders, 5–70 weight percent, preferably 10–50 weight percent, in emulsifiable concentrates, and 0.5–20 weight percent, preferably 1–10 weight percent in dust formulation.

Thus, a wettable powder or an emulsifiable concentrate produced thereto is diluted with water to a specified concentration and thereby, it is used as a liquid suspension or a liquid emulsion for treating the soils or the foliars leaf. Further, a dust formulation is directly used for the soil treatment or the foliar treatment.

The non-limiting examples for the herbicidal and plant growth regulating, fungicidal compositions are illustrated as follows:

EXAMPLE 5

Wettable Powder

| | Parts by weight |
|---|---|
| Compound 1 | 40 |
| Diatomaceous earth | 30 |
| Sodium alkylsulfate | 8 |
| Talc | 22 |

These are mixed homogeneously and reduced to fine particles. Consequently, wettable powder containing 40% of active ingredient is obtained. In practical use, it is diluted to a certain concentration with water and is sprayed as a suspension.

EXAMPLE 6

Emulsifiable Concentrate

| | Parts by weight |
|---|---|
| Compound 2 | 50 |
| Xylene | 30 |
| Dimethylformamide | 15 |
| Polyoxyethylene phenylether | 5 |

These are mixed and dissolved.

Consequently, emulsifiable concentrate containing 50% of the active ingredient is obtained. In practical use, it is diluted to certain concentration with water and then is sprayed as an emulsion.

EXAMPLE 7

Dust Formulation

| | Parts by weight |
|---|---|
| Compound 3 | 10 |
| Talc | 38 |
| Bentonite | 10 |
| Clay | 37 |
| Sodium alkylsulfate | 5 |

These are mixed homogeneously and reduced to fine particles. Fine particles is made into granules having the diameter in the range of 0.5–1.0 mm by granulator.

Consequently, dust formulation containing 10% of the active ingredient is obtained. In practical use it is directly applied.

The compounds listed in Table 1 possess superior herbicidal and plant growth regulating activities compared to known compounds, further fungicidal activity.

Furthermore, it must be stressed that the compounds of this invention having most superior herbicidal activity are one according to the above-mentioned general formula (IV) in which $R_1$ and $R_2$ are alkyl having 2 to 3 carbon atoms, $R_3$ is ethyl or allyl, when A is carbonyl R is phenyl or phenyl substituted with halogene, methyl, methoxy or nitro, when A is sulfonyl R is methyl, phenyl or phenyl substituted with halogene, methyl or methoxy.

The superior herbicidal, plant growth regulating and fungicidal effects of the novel compounds of this invention are clearly illustrated by the following tests.

As a compound for the comparison, 3-(N-ethoxyacetoimidoyl)-4-hydroxy-6-methyl-α-pyrone which is described in the Specification of Japanese Patent Publication No. 16916/1971 was employed.

TEST 1

TEST FOR PREVENTING SEED GERMINATION OF GRASS WEEDS IN FARM LAND

A vat having 780 cm² of surface area and containing packed soils and a seed mixture of grass weeds, i.e. large crab-grass and common purslane was prepared. In a stage of initiating germination of seeds of these grass weeds, the emulsifiable concentrate which was prepared in similar manner to Example 6 and was diluted with water to a specified concentration, and the resulting diluted emulsion was sprayed over the surface of the soils in the vat with soil treatment. In the course of 25th day after the treatment, a growth state of the grass weeds was investigated. A judging standard for the growth state was classified as six grades in the range of 0–5 which has the following meanings:

0 : no effect
1 : a few slightly burnt spots
2 : marked damage to leaves
3 : some leaves and parts of stalks partially dead 4 : plant partially destroyed
5 : plant completely destroyed or no germination
The results were shown in Table 2.

Table 2

| Test Compound No. | Amount of effective component (g/10 a.) | Growth state of plants large crab-grass | common purslane |
|---|---|---|---|
| 1 | 250 | 5 | 1 |
|   | 125 | 4 | 0 |
|   | 62.5 | 3 | 0 |
| 3 | 250 | 5 | 0 |
|   | 125 | 4 | 0 |
|   | 62.5 | 3 | 0 |
| 4 | 250 | 5 | 0 |
|   | 125 | 4 | 0 |
|   | 62.5 | 3 | 0 |
| 5 | 250 | 5 | 1 |
|   | 125 | 5 | 0 |
|   | 62.5 | 4 | 0 |
| 7 | 250 | 5 | 0 |
|   | 125 | 4 | 0 |
|   | 62.5 | 3 | 0 |
| 8 | 250 | 5 | 0 |
|   | 125 | 4 | 0 |
|   | 62.5 | 3 | 0 |
| 11 | 250 | 5 | 0 |
|   | 125 | 4 | 0 |
|   | 62.5 | 4 | 0 |
| 12 | 250 | 5 | 0 |
|   | 125 | 4 | 0 |
|   | 62.5 | 3 | 0 |
| 13 | 250 | 5 | 1 |
|   | 125 | 5 | 0 |
|   | 62.5 | 5 | 0 |
| 14 | 250 | 5 | 1 |
|   | 125 | 5 | 0 |
|   | 62.5 | 4 | 0 |
| 17 | 250 | 5 | 0 |
|   | 125 | 5 | 0 |
|   | 62.5 | 4 | 0 |
| 18 | 250 | 5 | 0 |
|   | 125 | 5 | 0 |
|   | 62.5 | 4 | 0 |
| 19 | 250 | 5 | 1 |
|   | 125 | 4 | 0 |
|   | 62.5 | 4 | 0 |
| 20 | 250 | 5 | 0 |
|   | 125 | 4 | 0 |
|   | 62.5 | 3 | 0 |
| 22 | 250 | 5 | 1 |
|   | 125 | 5 | 0 |
|   | 62.5 | 4 | 0 |
| 23 | 250 | 5 | 0 |
|   | 125 | 4 | 0 |
|   | 62.5 | 3 | 0 |
| 24 | 250 | 5 | 1 |
|   | 125 | 5 | 0 |
|   | 62.5 | 5 | 0 |
| 25 | 250 | 5 | 0 |
|   | 125 | 5 | 0 |
|   | 62.5 | 5 | 0 |
| 26 | 250 | 5 | 0 |
|   | 125 | 4 | 0 |
|   | 62.5 | 3 | 0 |
| 27 | 250 | 5 | 0 |
|   | 125 | 4 | 0 |
|   | 62.5 | 3 | 0 |
| 30 | 250 | 5 | 0 |
|   | 125 | 4 | 0 |
|   | 62.5 | 3 | 0 |
| 31 | 250 | 5 | 1 |
|   | 125 | 4 | 0 |
|   | 62.5 | 4 | 0 |
| 32 | 250 | 5 | 0 |
|   | 125 | 4 | 0 |
|   | 62.5 | 3 | 0 |
| 33 | 250 | 5 | 1 |
|   | 125 | 5 | 0 |
|   | 62.5 | 4 | 0 |
| 34 | 250 | 5 | 1 |
|   | 125 | 5 | 0 |
|   | 62.5 | 4 | 0 |
| 35 | 250 | 5 | 1 |
|   | 125 | 5 | 0 |
|   | 62.5 | 4 | 0 |
| Compound for the comparison | 250 | 5 | 1 |
|   | 125 | 3 | 0 |
|   | 62.5 | 1 | 0 |

TEST 2

FOLIAR TREATMENT TEST

Soils was packed in a vat having 780 cm$^2$ of surface area and the seeds of large crab-grass and smooth pigweed were sowed in the soil and a covering soils was softly laid upon it and those seeds were made to grow in a greenhouse. When these plants were grown to a stage of sprouting the secondary leaf or the fourth leaf, an emulsifiable concentrate of test compound was prepared by the similar method of Example 6 was diluted with water to a specified concentration and stems and leaves were treated by spraying 100 l/10 a. of amount of the resulting diluted emulsion. In the course of three weeks after the spraying treatment, the growth of the plants was investigated. The results were shown in Table 3 with the values of 0–5 which had the same meaning as those of Test 2.

Table 3

| Test Compound No. | Amount of effective component (g/10 a.) | Growth state of plants large crab-grass | smooth pigweed |
|---|---|---|---|
| 1 | 500 | 5 | 0 |
|   | 250 | 4 | 0 |
|   | 125 | 2 | 0 |
| 3 | 500 | 5 | 0 |
|   | 250 | 4 | 0 |
|   | 125 | 3 | 0 |
| 4 | 500 | 5 | 0 |
|   | 250 | 4 | 0 |
|   | 125 | 3 | 0 |
| 5 | 500 | 5 | 0 |
|   | 250 | 4 | 0 |
|   | 125 | 4 | 0 |
| 7 | 500 | 4 | 0 |
|   | 250 | 3 | 0 |
|   | 125 | 2 | 0 |
| 8 | 500 | 5 | 1 |
|   | 250 | 4 | 0 |
|   | 125 | 4 | 0 |
| 11 | 500 | 4 | 0 |
|   | 250 | 4 | 0 |
|   | 125 | 2 | 0 |
| 12 | 500 | 4 | 0 |
|   | 250 | 4 | 0 |
|   | 125 | 3 | 0 |
| 13 | 500 | 5 | 1 |
|   | 250 | 5 | 0 |
|   | 125 | 4 | 0 |
|   | 500 | 5 | 0 |

Table 3-continued

| Test Compound No. | Amount of effective component (g/10 a.) | Growth state of plants large crab-grass | smooth pigweed |
|---|---|---|---|
| 14 | 250 | 4 | 0 |
|  | 125 | 3 | 0 |
| 17 | 500 | 4 | 0 |
|  | 250 | 4 | 0 |
|  | 125 | 3 | 0 |
| 18 | 500 | 4 | 0 |
|  | 250 | 4 | 0 |
|  | 125 | 2 | 0 |
| 19 | 500 | 5 | 1 |
|  | 250 | 4 | 0 |
|  | 125 | 2 | 0 |
| 20 | 500 | 4 | 0 |
|  | 250 | 4 | 0 |
|  | 125 | 2 | 0 |
| 22 | 500 | 4 | 0 |
|  | 250 | 4 | 0 |
|  | 125 | 2 | 0 |
| 23 | 500 | 5 | 0 |
|  | 250 | 4 | 0 |
|  | 125 | 3 | 0 |
| 24 | 500 | 5 | 1 |
|  | 250 | 5 | 0 |
|  | 125 | 4 | 0 |
| 25 | 500 | 5 | 0 |
|  | 250 | 4 | 0 |
|  | 125 | 4 | 0 |
| 26 | 500 | 5 | 0 |
|  | 250 | 4 | 0 |
|  | 125 | 3 | 0 |
| 27 | 500 | 5 | 0 |
|  | 250 | 4 | 0 |
|  | 125 | 3 | 0 |
| 30 | 500 | 5 | 0 |
|  | 250 | 4 | 0 |
|  | 125 | 3 | 0 |
| 31 | 500 | 5 | 0 |
|  | 250 | 4 | 0 |
|  | 125 | 4 | 0 |
| 32 | 500 | 5 | 0 |
|  | 250 | 4 | 0 |
|  | 125 | 3 | 0 |
| 33 | 500 | 5 | 0 |
|  | 250 | 4 | 0 |
|  | 125 | 3 | 0 |
| 34 | 500 | 5 | 1 |
|  | 250 | 4 | 0 |
|  | 125 | 4 | 0 |
| 35 | 500 | 5 | 0 |
|  | 250 | 4 | 0 |
|  | 125 | 4 | 0 |
| Compound for the comparison | 500 | 3 | 0 |
|  | 250 | 2 | 0 |
|  | 125 | 1 | 0 |

TEST 3

TEST FOR TREATING SOILS WITH WATER STAGNATION PROCESS

Soils was packed in a pot and about 15 grains of barnyard grass seeds were sowed in it and a covering soils was softly laid upon them and those seeds were made to grown in a greenhouse. In the occasion that the seeds were germinated and the plants were grown to a stage of spouting the first leaf, the said pot was dipped with a water stagnated container having 3 cm of water depth. Each emulsifiable concentrate which contains above mentioned each compound and was prepared in similar manner to Example 6 was respectively diluted with water to a specified concentrate and a definite amount of each diluted emulsion was respectively poured into the said pot. In the course of 14th day after the water stagnation treatment, the growth state of barnyard grass was investigated. The results were shown in Table 4 with the values of 0–5 which had the same meanings as those of Test 4.

Table 4

| Test Compound No. | Amount of effective component (g/10 a.) 125 | 62.5 | 31.3 |
|---|---|---|---|
| 1 | 5 | 4 | 4 |
| 3 | 5 | 5 | 4 |
| 4 | 5 | 5 | 4 |
| 5 | 5 | 5 | 5 |
| 7 | 5 | 4 | 3 |
| 8 | 5 | 5 | 5 |
| 11 | 5 | 5 | 4 |
| 12 | 5 | 4 | 3 |
| 13 | 5 | 5 | 5 |
| 14 | 5 | 5 | 5 |
| 17 | 5 | 5 | 5 |
| 18 | 5 | 5 | 4 |
| 19 | 5 | 4 | 3 |
| 20 | 5 | 5 | 4 |
| 22 | 5 | 4 | 3 |
| 23 | 5 | 5 | 4 |
| 24 | 5 | 5 | 5 |
| 25 | 5 | 5 | 5 |
| 26 | 5 | 5 | 5 |
| 27 | 5 | 4 | 4 |
| 30 | 5 | 5 | 4 |
| 31 | 5 | 5 | 4 |
| 32 | 5 | 5 | 3 |
| 33 | 5 | 5 | 5 |
| 34 | 5 | 5 | 4 |
| 35 | 5 | 5 | 4 |
| The compound for the comparison | 4 | 3 | 1 |
| Untreated | 0 | 0 | 0 |

TEST 4

TEST FOR TESTING SELECTIVE HERBICIDAL ACTIVITY

Soils was packed in a vat having 780 cm² of surface area and those seeds of barnyard grass, beet (*Beta vulgaris*), radish (*Rephanus stativus*), cucumber (*Cumumis sativus*), rad bean, and tomato (*Lycopersicon esculentum*) and then, a covering soils was softly laid upon them and those seeds were made to germinate in a greenhouse. In occasion that those seeds were germinated and grown to a crop having a height of 5 to 8 cm, the emulsifiable concentrate of test compounds prepared in similar manner to Example 6 was diluted with water to a specified concentration and the resulting diluted emulsion by 100 l/10 a. of feed rate was respectively sprayed over stems and leaves of those crop seedlings. In the course of the 14th day after above spraying treatment, the growth state of those crops was investigated with the "naked eye's judgement".

The results were shown in Table 5 with the values of 0–5 which have the same meaning as those of Test 1.

Table 5

| Test Compound No. | Amount of effective component (g/10 a.) | Poaceous plant Barnyard grass | Broadleaf plant Beet | Cucumber | Radish | Red bean | Tomato |
|---|---|---|---|---|---|---|---|
| 1 | 150 | 4 | 0 | 0 | 0 | 0 | 0 |
| 3 | 150 | 4 | 0 | 0 | 0 | 0 | 0 |
| 4 | 150 | 5 | 0 | 0 | 0 | 0 | 1 |
| 5 | 150 | 5 | 0 | 0 | 0 | 0 | 0 |
| 7 | 150 | 4 | 0 | 0 | 0 | 0 | 0 |
| 8 | 150 | 5 | 0 | 0 | 1 | 0 | 0 |
| 11 | 150 | 4 | 0 | 0 | 0 | 0 | 0 |
| 12 | 150 | 5 | 0 | 0 | 0 | 0 | 1 |
| 13 | 150 | 5 | 0 | 0 | 0 | 0 | 0 |
| 14 | 150 | 5 | 0 | 0 | 0 | 0 | 0 |
| 17 | 150 | 4 | 0 | 0 | 0 | 0 | 0 |
| 18 | 150 | 4 | 0 | 0 | 0 | 0 | 0 |
| 19 | 150 | 5 | 0 | 0 | 0 | 0 | 0 |
| 20 | 150 | 4 | 0 | 0 | 0 | 0 | 0 |
| 22 | 150 | 4 | 0 | 0 | 0 | 0 | 0 |
| 23 | 150 | 5 | 0 | 0 | 0 | 1 | 0 |
| 24 | 150 | 5 | 1 | 0 | 0 | 0 | 0 |
| 25 | 150 | 4 | 0 | 0 | 0 | 0 | 0 |
| 26 | 150 | 5 | 0 | 0 | 0 | 0 | 0 |
| 27 | 150 | 5 | 0 | 0 | 0 | 1 | 0 |
| 30 | 150 | 5 | 0 | 0 | 0 | 0 | 1 |
| 31 | 150 | 5 | 0 | 0 | 0 | 0 | 0 |
| 32 | 150 | 5 | 0 | 0 | 0 | 0 | 0 |
| 33 | 150 | 5 | 1 | 0 | 0 | 0 | 0 |
| 34 | 150 | 5 | 0 | 0 | 0 | 0 | 0 |
| 35 | 150 | 5 | 0 | 0 | 0 | 0 | 0 |
| Compound for the comparison | 150 | 3 | 0 | 0 | 0 | 0 | 0 |
| Untreated | — | 0 | 0 | 0 | 0 | 0 | 0 |

TEST 5

TEST FOR CONTROLLING GROWTH OF LAWN

A lawn seedlings (species : Highland Bent) in a growing stage which was planted in a pot having 9 cm of diameter was moved with a small sizer of mower, so as it may be about 1.5 cm high. In the course of the second day after above moving step, the each emulsifiable concentrate which contained test compound and was prepared in similar manner to Example 6 was respectively diluted with water to a specified concentration and the each diluted emulsion by 100 l/10 a. of feed amount was respectively sprayed over each mowed lawn seedlings. In the course of 5th day and 12th day after the spraying treatment, both investigations were carried out for measuring the grass heights. This investigation results were set forth in Table 6. (Note : above experiment was carried for each one testing zone consisting of three section units)

Table 6

| Test Compound No. | Amount of effective component for the treatment (g/10 a.) | Grass height after 5 days (cm) | Grass height after 12 days (cm) |
|---|---|---|---|
| 8 | 50 | 1.4 | 1.7 |
|   |    | 1.6 | 1.7 |
|   |    | 1.6 | 1.9 |
|   | 25 | 1.8 | 3.0 |
|   |    | 1.5 | 2.7 |
|   |    | 1.7 | 3.0 |
| 13 | 50 | 1.3 | 1.6 |
|    |    | 1.5 | 1.5 |
|    |    | 1.5 | 1.5 |
|    | 25 | 1.7 | 2.8 |
|    |    | 2.0 | 3.0 |
|    |    | 2.0 | 3.0 |
|    | 50 | 1.5 | 1.7 |
|    |    | 1.8 | 1.9 |
|    |    | 1.6 | 1.6 |

Table 6-continued

| Test Compound No. | Amount of effective component for the treatment (g/10 a.) | Grass height after 5 days (cm) | Grass height after 12 days (cm) |
|---|---|---|---|
| 25 |    |     |     |
|    | 25 | 2.0 | 2.7 |
|    |    | 1.6 | 2.9 |
|    |    | 2.0 | 3.1 |
| Untreated pot | — | 3.8 | 7.0 |
|   |   | 3.5 | 7.5 |
|   |   | 3.8 | 7.0 |

TEST 6

FUNGICIDAL TEST

Seeds of cucumber (species : *Cucumis sativus*, variety, *Sagami Hampaku*) were sowed in a pot and its seedlings were made to grow. In the case of spreading its cotyledons, the emulsifiable concentrate prepared in similar manner to Example 6 was diluted with water to a specified concentration and 10 ml of the resulting diluted emulsion was poured in the soils of the pot. On the next day, *Rhizoctonia solani* which was cultured in a culture medium consisting of wheat brans and chaffs was inoculated on the cucumber seedlings. In the course of the fifth day after the inoculating step, the seedlings which are suffered from a disease infected with this fungus were investigated and thereby a preventive value was calculated. (Note : Above experiment was carried out for each one zone consisting of two pots) Average values of the investigating results are set forth in Table 7.

Table 7

| Compound No. for the experiment | Concentration of effective component (ppm) | Average preventive value (%) |
| --- | --- | --- |
| 12 | 500 | 90 |
| 13 | 500 | 90 |
| 14 | 500 | 89 |
| 20 | 500 | 88 |
| 32 | 500 | 100 |
| 33 | 500 | 100 |

What is claimed is:
1. A compound of the formula wherein $R_1$ is alkyl having from 2 to 6 carbon atoms or phenyl;
$R_2$ is alkyl having from 2 to 6 carbon atoms or phenyl;
$R_3$ is alkyl having from 1 to 10 carbon atoms or alkenyl having six or less carbon atoms or alkynyl having six or less carbon atoms;
R is alkyl having from 1 to 20 carbon atoms, or phenyl or phenyl substituted with halogen, methyl, methoxy or nitro group;
A is carbonyl or sulfonyl.

2. A compound according to claim 1 in which $R_1$ and $R_2$ are alkyl having from 2 to 3 carbon atoms, $R_3$ is ethyl or allyl, R is phenyl or phenyl substituted with chlorine, methyl, methoxy or nitro where A is carbonyl, or R is methyl, phenyl or phenyl substituted with chlorine, methyl or methoxy where A is sulfonyl.

3. A compound according to claim 1 in which $R_1$, $R_2$ and $R_3$ are ethyl, R is phenyl and A is carbonyl.

4. A compound according to claim 1 in which $R_1$, $R_2$ and $R_3$ are ethyl, R is 4-chlorophenyl and A is carbonyl.

5. A compound according to claim 1 in which $R_1$, $R_2$ and $R_3$ are ethyl, R is methyl and A is sulfonyl.

* * * * *